(12) United States Patent
Warriner et al.

(10) Patent No.: US 8,151,445 B1
(45) Date of Patent: Apr. 10, 2012

(54) STENT LOADING MECHANISM

(76) Inventors: Jeremiah J. Warriner, Laveen, AZ (US); Ed Goff, Phoenix, AZ (US); Justin Knight, Tempe, AZ (US)

( * ) Notice: Subject to any disclaimer, the term of this patent is extended or adjusted under 35 U.S.C. 154(b) by 786 days.

(21) Appl. No.: 12/265,472

(22) Filed: Nov. 5, 2008

Related U.S. Application Data

(60) Provisional application No. 60/985,726, filed on Nov. 6, 2007.

(51) Int. Cl.
*B23P 21/00* (2006.01)
*B23P 19/02* (2006.01)
(52) U.S. Cl. .......................... 29/719; 29/235
(58) Field of Classification Search ................ 29/505, 29/506, 508, 428, 235, 234, 243.517, 243.518, 29/243.519, 243.523, 243.528, 281.4, 719; 100/232, 291; 72/402
See application file for complete search history.

(56) References Cited

U.S. PATENT DOCUMENTS

| | | | |
|---|---|---|---|
| 6,968,607 B2 * | 11/2005 | Motsenbocker | 29/505 |
| 7,886,661 B1 * | 2/2011 | Goff et al. | 100/232 |
| 7,963,142 B2 * | 6/2011 | Goff | 72/402 |

* cited by examiner

*Primary Examiner* — John C Hong
(74) *Attorney, Agent, or Firm* — Parsons & Goltry; Robert A. Parsons; Michael W. Goltry

(57) ABSTRACT

A translating radial compression and holding mechanism includes radially movable dies defining a cylindrical cavity with movable radius. Apparatus coupled to the dies for sequenced lateral movement of the dies in a first direction and an opposite direction, substantially parallel to the central cavity to convey the compressed article along the axis of the central cavity. A compliant tube with a central opening larger than an article to be held, a case surrounding the tube along the longitudinal axis, and a plurality of cylindrical bushings positioned between the outer case and the tube. Mechanism associated with the tube for compressing the tube along the longitudinal axis to reduce the diameter of the central opening for gripping a second article residing therein, and the cylindrical cavity of the dies being positioned in axial alignment with the central opening of the tube.

20 Claims, 4 Drawing Sheets

Die Motion to Convey Stent

STENT LOADING MECHANISM

CROSS REFERENCE TO RELATED APPLICATION

This application claims the benefit of U.S. Provisional Patent Application No. 60/985,726, filed 6 Nov. 2008.

FIELD OF THE INVENTION

This invention relates to medical device manufacturing equipment.

More particularly, the present invention relates to stent preparation and encasement.

BACKGROUND OF THE INVENTION

As part of the manufacture of medical self-expanding stents, stents must be compressed radially and loaded into a delivery catheter. Typically the stents are compressed down using a radial compression mechanism to a precise diameter. Then with the delivery catheter secured on one side of the compression mechanism the stent is pushed through the compression mechanism into the catheter with a rod-like device.

A deficiency of this method is that the force required to translate the stent from inside the compression mechanism into the catheter can be quite high, especially with a long stent. Since the push force is concentrated primarily on the end of the stent, the stent can be easily damaged. In some cases, to prevent damage to the stent during translation into the delivery catheter or other sheath, limiting the length of stents that can be designed and marketed becomes necessary.

Another challenge with the stent loading process is holding the delivery catheter in such a way that it is aligned precisely with the radial compression mechanism, is not deformed into a non-cylindrical shape, and the ability to accommodate a range of diameters. Typically, a hinged clamp with two v-shaped grooves or precisely cut semi-circles is used to hold the catheter in place. The v-shape grooves accommodate a wide range of diameters, but have a tendency to deform the catheter into a square shape. The precisely cut semi-circles keep the product round, but must be customized for each diameter of product and small variations of catheter diameter greatly affect the holding force.

Generally, the catheter clamp is aligned relative to the radial compression mechanism with an adjustable mechanism. It is sometimes difficult to precisely adjust alignment and over time the adjustment may change. To compensate for this, catheters are often manufactured with a funnel on the tip to help guide the stent. This funnel is typically removed in a subsequent manufacturing step.

It would be highly advantageous, therefore, to remedy the foregoing and other deficiencies inherent in the prior art.

An object of the present invention is to provide a new and improved stent loading mechanism.

Another object of the present invention is to provide a stent loading mechanism which will not damage the stent and does not limit stent dimensions.

Yet another object of the present invention is to provide a stent loading mechanism which will align a delivery catheter without deformation thereof.

SUMMARY OF THE INVENTION

Briefly, to achieve the desired objects of the instant invention in accordance with a preferred embodiment thereof, a translating radial compression and article holding mechanism is provided that includes a plurality of radially movable elongated dies arranged to define a central cylindrical cavity with variable radius. The dies are mounted for radial movement between an open article receiving orientation wherein a compressible article is receivable in the central cylindrical cavity and a closed article compressing orientation. Apparatus is coupled to the dies for sequenced lateral movement of the dies in a first direction and an opposite direction, substantially parallel to the central cavity to convey the compressed article along the axis of the central cavity.

Briefly, the desired objects of the instant invention are further achieved in accordance with a specific embodiment of a translating radial compression and article holding mechanism that includes an elongated compliant tube with a central opening along a longitudinal axis and having a diameter larger than the diameter of an article to be held. An outer case surrounds the compliant tube along the longitudinal axis thereof, and a plurality of cylindrical bushings are positioned between the outer case and the compliant tube and spaced apart along the length of the compliant tube. Compressing mechanism is associated with one end of the compliant tube and designed to compress the compliant tube along the longitudinal axis to reduce the diameter of the central opening for gripping a second article residing therein.

The desired objects of the instant invention are further achieved in accordance with an embodiment of a method of compressing a stent and inserting it in a catheter including the steps of providing translating radial compression mechanism including a plurality of radially movable dies defining a central cylindrical cavity, inserting a compressible stent longitudinally into the central cylindrical cavity, radially moving the plurality of dies to compress the stent, providing holding mechanism including a compliant tube with a central opening along a longitudinal axis having a diameter larger than the diameter of a catheter to be held, and compressing mechanism associated with one end of the compliant tube and designed to compress the compliant tube along the longitudinal axis to reduce the diameter of the central opening for gripping the catheter therein, placing a catheter in the central opening of the compliant tube and activating the compressing mechanism to grip the catheter in the central opening, aligning the central opening of the elongated compliant tube with the central cylindrical cavity of the plurality of radially movable elongated dies and moving the compressed stent into the catheter gripped in the compliant tube.

The desired objects of the instant invention are further achieved in accordance with a specific embodiment of a method of compressing a stent and inserting it in a catheter including the steps of providing translating radial compression mechanism including a plurality of radially movable dies defining a central cylindrical cavity, and apparatus coupled to the dies for laterally moving the dies independently in a first direction substantially parallel to the central cavity and moving the dies collectively in an opposite direction to convey a compressed stent along the axis of the central cavity, inserting a compressible stent longitudinally at least partially into the central cylindrical cavity, activating the apparatus coupled to the dies to move the dies independently in the first direction to move the stent fully into the central cylindrical cavity, and radially moving the plurality of dies to compress the stent, providing holding mechanism including a compliant tube with a central opening along a longitudinal axis having a diameter larger than the diameter of a catheter to be held, and compressing mechanism associated with one end of the compliant tube and designed to compress the compliant tube along the longitudinal axis to reduce the diameter of the central opening for gripping the catheter therein, placing a catheter in the central opening of the compliant tube and activating the compressing mechanism to grip the catheter in the central opening, aligning the central opening of the elongated compliant tube with the central cylindrical cavity of the plurality of radially movable elongated dies, and activating the apparatus coupled to the dies to move the dies collectively and move the compressed stent into the catheter gripped in the compliant tube.

BRIEF DESCRIPTION OF THE DRAWINGS

The foregoing and further and more specific objects and advantages of the invention will become readily apparent to those skilled in the art from the following detailed description of a preferred embodiment thereof, taken in conjunction with the drawings in which.

DETAILED DESCRIPTION OF A PREFERRED EMBODIMENT

Figure 1:
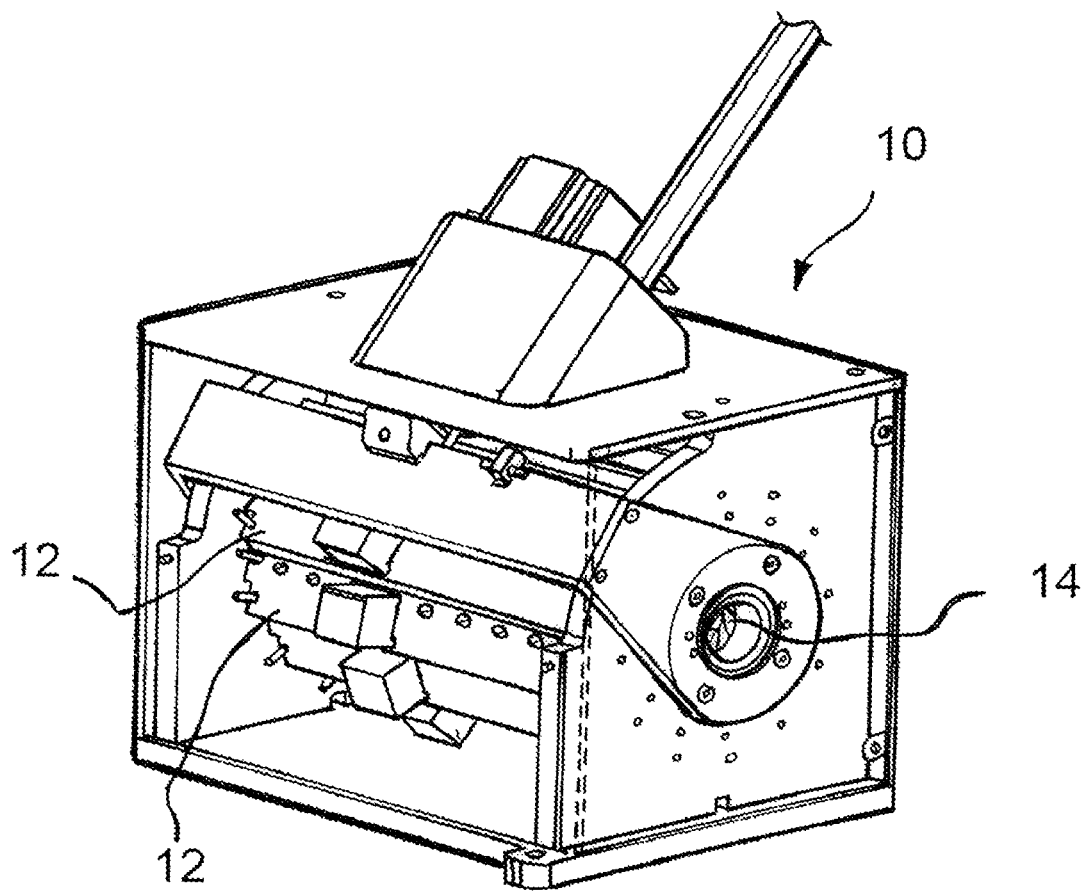
FIG. 1 is perspective of view of a stent translating compression mechanism according to the present invention.

Turning now to the drawings in which like reference characters indicate corresponding elements throughout the several views, attention is directed to FIG. 1 which illustrates a translating radial compression mechanism generally designated 10. Translating radial compression mechanism 10 can be, for example, substantially similar to that disclosed in U.S. Pat. No. 6,968,607 or Pending Applications Nos. 11/842,882, 12/027,059, and 12/101,550, herein incorporated by reference, which consist of a plurality of dies 12 arranged to create an approximately cylindrical opening 14, used to uniformly compress a stent down to a smaller diameter. In the present invention as illustrated in FIG. 1, when the stent reaches the diameter at which it is to be loaded into a catheter, dies 12 of translating compression mechanism 10 are actuated in an axis that is parallel to the stent loading path in such a way so as to reduce or eliminate the friction between the stent and the dies and to propel the stent through translating radial compression mechanism 10.

Figure 2:
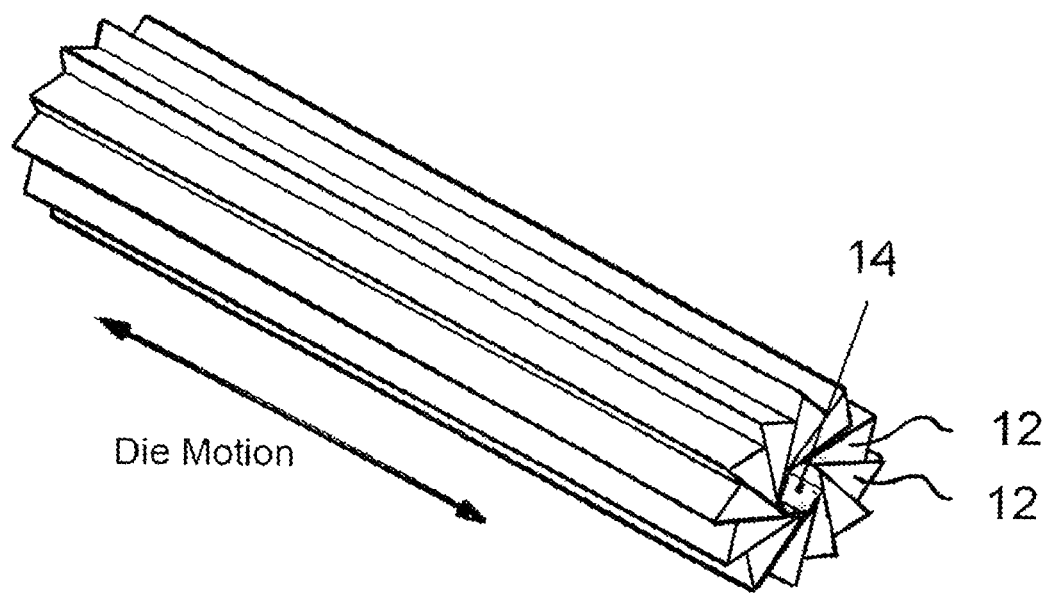
FIG. 2 is a simplified schematic in perspective of a translating compression die assembly according to the present invention.

The stent is translated through mechanism 10 by a sequenced actuation of dies 12 between a forward and a rearward position as shown in FIG. 2. As a specific example, one die is independently actuated a small distance, for example 0.005 to 0.030 inches, in the direction opposite the stent loading direction, from a forward position to a rearward position. Since all the other dies remain in place the stent will tend to remain stationary with the other dies. Each of the dies in turn is independently actuated to a rearward position while the stent remains in place. When all of the dies have moved to the rearward position, all the dies move forward to the forward position in unison, propelling the stent forward. This procedure is repeated rapidly to convey the stent toward and into a catheter aligned therewith.

As another example of sequenced actuation of the dies, the dies are moved in small groups (for example 3 of a total of 12) in the direction opposite the stent loading direction, from a forward position to a rearward position. Since all the other dies remain in place the stent will tend to remain stationary with the other dies. Each of the groups in turn is independently actuated to a rearward position while the stent remains in place. When all of the dies have moved to the rearward position, all the dies move forward to the forward position in unison, propelling the stent forward. This procedure is repeated rapidly to convey the stent toward and into the catheter aligned therewith.

As yet another example of sequenced actuation of the dies, the dies are moved in two groups, each including half of the total number of dies. One group moves in the direction opposite the stent loading direction, from a forward position to a rearward position, while the other group simultaneously moved in the direction opposite from the first group. This procedure is repeated rapidly to eliminate the static friction between the stent and the dies, allowing a pushrod to easily propel the stent toward and into the catheter aligned therewith. There are many other possible sequences of die actuation that are advantageous.

Figure 3:
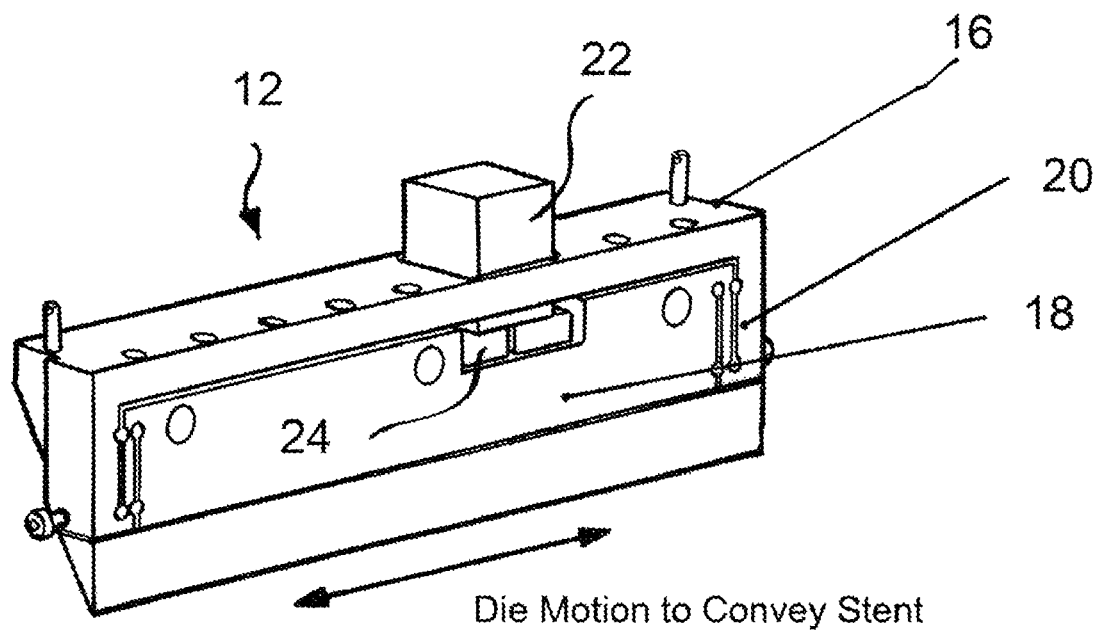
FIG. 3 is side view in perspective of a translating compression die according to the present invention.
Figure 4:
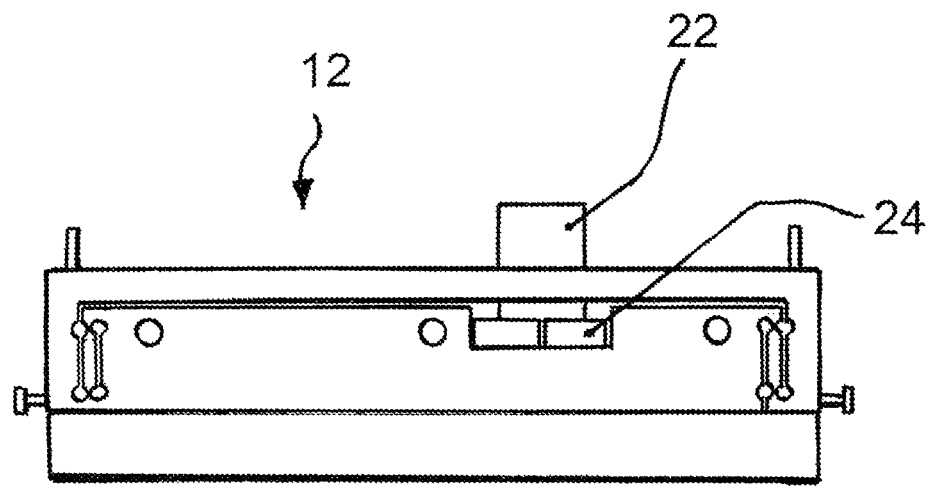
FIG. 4 is a side view of the translating die of FIG. 1.

There are many different methods that can be employed to provide dies 12 capable of movement in the manner described. Turning now to FIGS. 3 and 4, in a preferred embodiment each die 12 is formed with two sections, a stationary section 16 and translating section 18. Translating section 18 is connected to stationary section 16 by means of a flexure 20. Flexure 20 is designed to constrain translating section 18 to move in a substantially linear path along or parallel to the axis of central opening 14. Flexure 20 is also designed to be stiff in the axis perpendicular to the stent axis so that there is minimal deflection when the stent is being compressed.

There are many different methods that would be suitable to actuate the dies back and forth between the forward position and the rearward position. One method consists of mounting an electromagnet 22 on one of stationary section 16 and translating section 18 of each die 12 and two permanent magnets 24 on the other of stationary section 16 and translating section 18. The magnets are arranged so that when electrical current is applied to electromagnet 22 translating section 18 is propelled along the axis of the stent. When the current is reversed translating section 18 moves in the opposite direction. It will be understood that other apparatus for actuating the dies has been contemplated. For example the dies can be actuated by pneumatic actuators, electric solenoids and the like.

Figure 6:
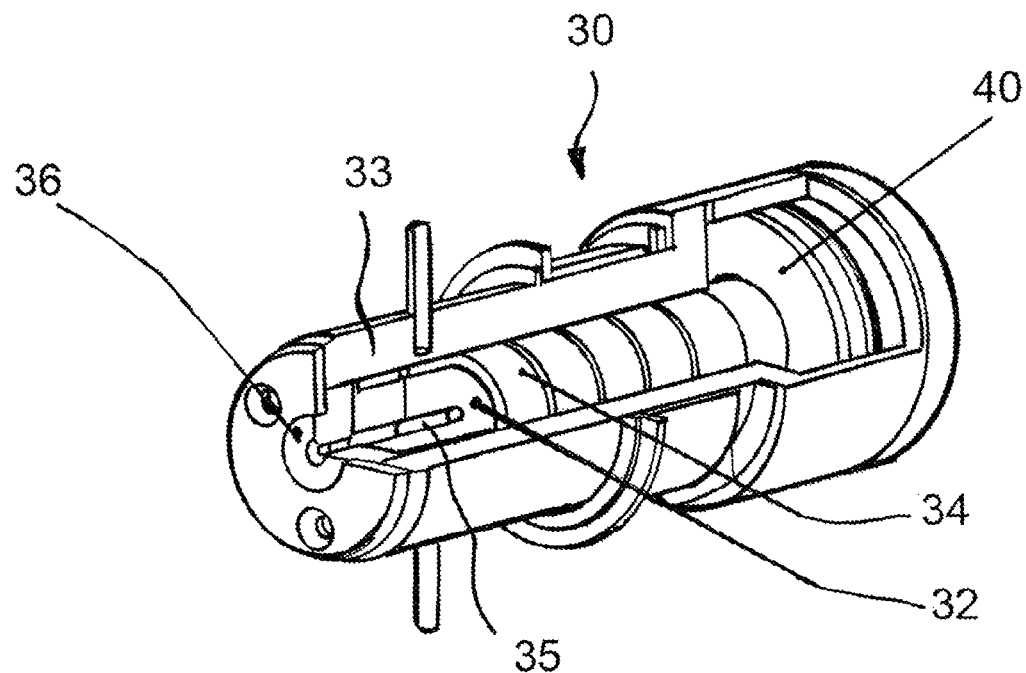
FIG. 6 is a perspective view of the catheter holder of FIG. 5 with portions thereof cutaway to illustrate internal components.
Figure 5:
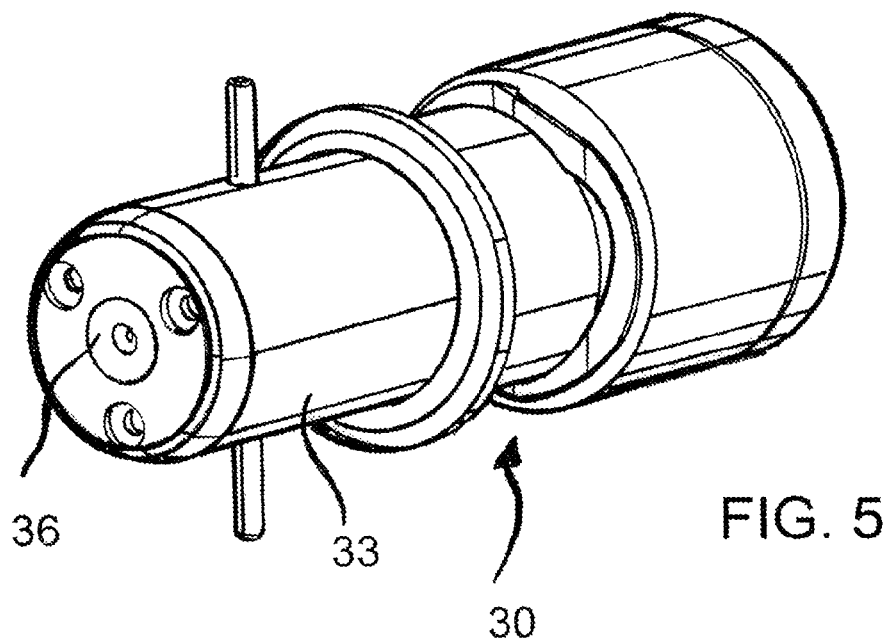
FIG. 5 is a perspective view of a catheter holder according to the present invention.

Turning now to FIGS. 5 and 6, a catheter holding mechanism 30 for holding a catheter in the stent loading process is illustrated. Catheter holding mechanism 30 consists of a compliant tube 32 with relatively thick walls constrained inside a rigid case 33. Compliant tube 32 has a center opening 35 sized to be larger than but close to the outside diameter of the catheter to be held. Compliant tube 32 is compressed along an axis parallel to center opening 35, causing compliant tube 32 to strain and reduce the diameter of center opening 35. By reducing the diameter of center opening 35 a catheter is securely gripped therein. Preferably, there are a series of bushings 34 between the interface of case 33 and compliant tube 32 to prevent portions of tube 32 from seizing on the bore and not allowing the axial force to be transmitted along the entire length of tube 32. Bushings 34 allow for the use of much longer lengths of compliant tubes which increases the gripping length on the catheter. The gripping force can be controlled by adjusting the axial actuation force. The axial actuation force can be generated by a pneumatic actuator 40 positioned adjacent an end of compliant tube 32.

Figure 7:
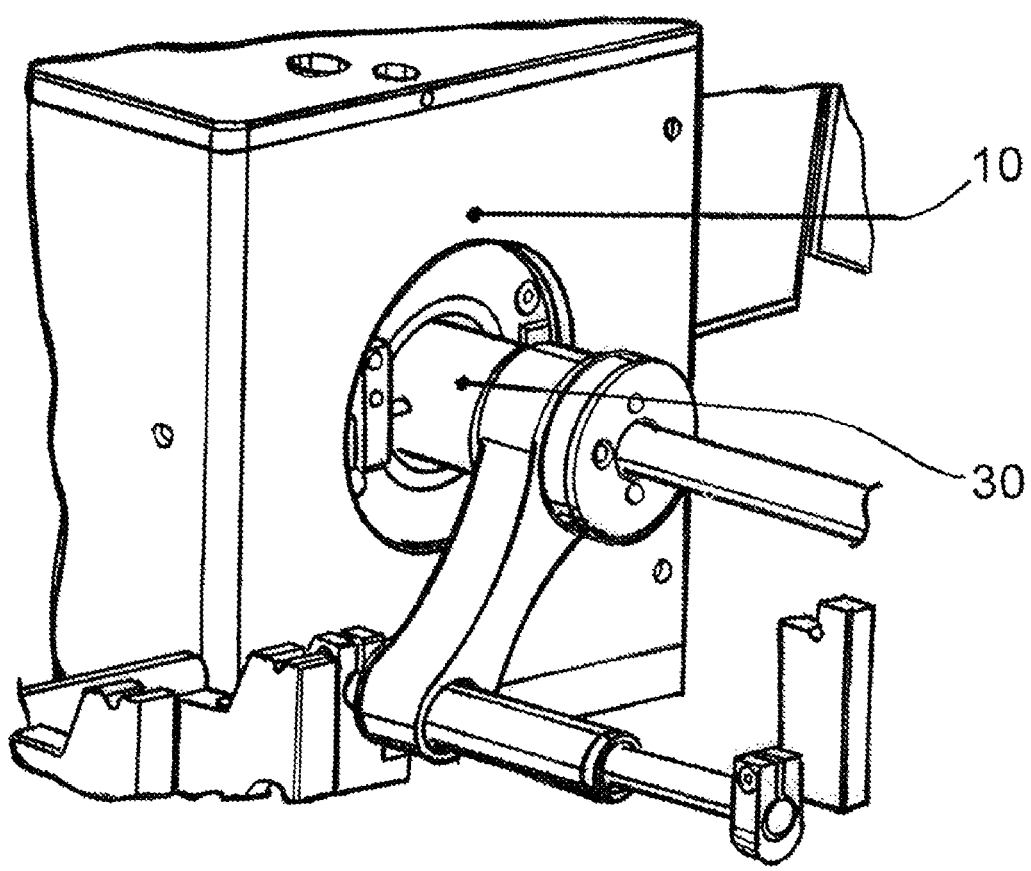
FIG. 7 is a partial perspective view of the translating compression mechanism with aligned catheter holder.

This method of gripping the catheter is a vast improvement over prior art because it holds the catheter in a cylindrical shape and accommodates a relatively wide range of diameters. Additionally, holding mechanism 30 can be outfitted with an alignment bushing 36 that is precisely positioned relative to radial compression mechanism 10 as can be seen in FIG. 7. Alignment bushing 36 can be sized specifically for the catheter and can include a funnel to guide the stent into the catheter, eliminating the need to incorporate a funnel into every catheter.

A variation of the catheter holding mechanism described above results in reduced forces to load the stent into the catheter. While the stent is being held in place by the compliant tube a portion of the tube is increased or decreased in diameter. This local deformation is caused to move down the length of the compliant tube in a wave-like fashion. The stent tends to move further into the catheter, following the wave-like motion. The process is similar to the method a snake uses to transport food through its digestive system.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same,

The invention claimed is:

1. A translating radial compression and article holding mechanism comprising:
    a plurality of radially movable elongated dies arranged to define a central cylindrical cavity with variable radius, the dies being mounted for radial movement between an open article-receiving orientation wherein a compressible article is receivable in the central cylindrical cavity and a closed article compressing orientation; and
    apparatus coupled to the dies for sequenced lateral movement of the dies in a first direction and an opposite direction, substantially parallel to the central cavity to convey a compressed article along the axis of the central cavity.

2. A translating radial compression and article holding mechanism as claimed in claim 1 wherein apparatus coupled to the dies for sequenced laterally movement includes the apparatus coupled to the dies for laterally moving the dies independently in a first direction substantially parallel to the central cavity and moving the dies collectively in an opposite direction to convey the compressed article along the axis of the central cavity.

3. A translating radial compression and article holding mechanism as claimed in claim 1 wherein each die of the plurality of dies includes an outer stationary section and an inner translating section.

4. A translating radial compression and article holding mechanism as claimed in claim 3 wherein the inner translating section is movably coupled to the outer stationary section by a flexure designed to constrain lateral movement to a substantially linear path substantially parallel to the central cavity.

5. A translating radial compression and article holding mechanism as claimed in claim 4 wherein the flexure is further designed to allow minimal deflection in an axis substantially perpendicular to the central cavity.

6. A translating radial compression and article holding mechanism as claimed in claim 1 wherein the apparatus coupled to the dies for laterally moving the dies includes magnets affixed to the outer stationary section and to the inner translating section, the magnets being activatable to provide the lateral movement.

7. A translating radial compression and article holding mechanism as claimed in claim 6 wherein the magnets include at least one electromagnet affixed to one of the outer stationary section and the inner translating section and at least one permanent magnet affixed to the other of the outer stationary section and the inner translating section.

8. A translating radial compression and article holding mechanism as claimed in claim 1 wherein the article holding mechanism includes an elongated compliant tube with a central opening along a longitudinal axis and having a diameter larger than the diameter of an article to be held, and compressing mechanism associated with one end of the compliant tube and designed to compress the compliant tube along the longitudinal axis to reduce the diameter of the central opening for gripping an article residing therein.

9. A translating radial compression and article holding mechanism as claimed in claim 8 wherein the article holding mechanism further includes an outer case surrounding the compliant tube along the longitudinal axis thereof, and a plurality of cylindrical bushings positioned between the outer case and the compliant tube and spaced apart along the length of the compliant tube.

10. A translating radial compression and article holding mechanism as claimed in claim 8 wherein the compressing mechanism includes a pneumatic actuator positioned adjacent an end of the compliant tube and designed to provide axial compressing force to the compliant tube.

11. A translating radial compression and article holding mechanism as claimed in claim 8 further including an alignment bushing with an opening therethrough positioned between the central cylindrical cavity defined by the plurality of dies and the central opening of the compliant tube, with the central cylindrical cavity, the opening through the alignment bushing, and the central opening all axially aligned.

12. A translating radial compression and article holding mechanism as claimed in claim 11 wherein the compressing mechanism includes a pneumatic actuator positioned adjacent an end of the compliant tube and designed to provide axial compressing force to the compliant tube.

13. A translating radial compression and article holding mechanism comprising:
    an elongated compliant tube with a central opening along a longitudinal axis and having a diameter larger than a diameter of an article to be held, an outer case surrounding the compliant tube along the longitudinal axis thereof, and a plurality of cylindrical bushings positioned between the outer case and the compliant tube and spaced apart along the length of the compliant tube; and
    compressing mechanism associated with one end of the compliant tube and designed to compress the compliant tube along the longitudinal axis to reduce the diameter of the central opening for gripping a second article residing therein.

14. A translating radial compression and holding mechanism comprising:
    a plurality of radially movable elongated dies arranged to define a central cylindrical cavity with variable radius, the dies being mounted for radial movement between an open article-receiving orientation wherein a compressible article is receivable in the central cylindrical cavity and a closed article-compressing orientation;

apparatus coupled to the dies for sequenced lateral movement of the dies in a first direction and an opposite direction, substantially parallel to the central cavity to convey a compressed article along the axis of the central cavity;

an elongated compliant tube with a central opening along a longitudinal axis and having a diameter larger than the diameter of a second article to be held, an outer case surrounding the compliant tube along the longitudinal axis thereof, and a plurality of cylindrical bushings positioned between the outer case and the compliant tube and spaced apart along the length of the compliant tube;

compressing mechanism associated with one end of the compliant tube and designed to compress the compliant tube along the longitudinal axis to reduce the diameter of the central opening for gripping a second article residing therein; and the central cylindrical cavity of the plurality of radially movable elongated dies being positioned in axial alignment with the central opening of the elongated compliant tube.

15. A translating radial compression and article holding mechanism as claimed in claim 14 wherein the apparatus coupled to the dies for sequenced lateral movement includes apparatus coupled to the dies for laterally moving the dies independently in a first direction substantially parallel to the central cavity and moving the dies collectively in an opposite direction to convey the compressed article along the axis of the central cavity.

16. A translating radial compression and article holding mechanism as claimed in claim 14 wherein each die of the plurality of dies includes an outer stationary section and an inner translating section.

17. A translating radial compression and article holding mechanism as claimed in claim 16 wherein the inner translating section is movably coupled to the outer stationary section by a flexure designed to constrain lateral movement to a substantially linear path substantially parallel to the central cavity.

18. A translating radial compression and article holding mechanism as claimed in claim 17 wherein the flexure is further designed to allow minimal deflection in an axis substantially perpendicular to the central cavity.

19. A translating radial compression and article holding mechanism as claimed in claim 14 wherein the apparatus coupled to the dies for laterally moving the dies includes magnets affixed to the outer stationary section and to the inner translating section, the magnets being activatable to provide the lateral movement.

20. A translating radial compression and article holding mechanism as claimed in claim 19 wherein the magnets include at least one electromagnet affixed to one of the outer stationary section and the inner translating section and at least one permanent magnet affixed to the other of the outer stationary section and the inner translating section.

* * * * *